(12) United States Patent
Sreedharala et al.

(10) Patent No.: US 12,280,031 B2
(45) Date of Patent: Apr. 22, 2025

(54) TERIFLUNOMIDE TOPICAL PHARMACEUTICAL COMPOSITIONS

(71) Applicant: APRAMITHA INNOVATIONS PRIVATE LIMITED, Telangana (IN)

(72) Inventors: Venkata Nookaraju Sreedharala, Hyderabad (IN); Ramdas Manakkote, Hyderabad (IN); Srikanth Kalakoti, Hyderabad (IN)

(73) Assignee: APRAMITHA INNOVATIONS PRIVATE LIMITED, Telangana (IN)

( * ) Notice: Subject to any disclaimer, the term of this patent is extended or adjusted under 35 U.S.C. 154(b) by 930 days.

(21) Appl. No.: 17/291,006

(22) PCT Filed: Nov. 5, 2019

(86) PCT No.: PCT/IN2019/050818
§ 371 (c)(1),
(2) Date: May 4, 2021

(87) PCT Pub. No.: WO2020/095319
PCT Pub. Date: May 14, 2020

(65) Prior Publication Data
US 2022/0040138 A1 Feb. 10, 2022

(30) Foreign Application Priority Data
Nov. 5, 2018 (IN) .............................. 201841041818

(51) Int. Cl.
*A61K 31/277* (2006.01)
*A61K 9/06* (2006.01)
*A61K 45/06* (2006.01)

(52) U.S. Cl.
CPC .............. *A61K 31/277* (2013.01); *A61K 9/06* (2013.01); *A61K 45/06* (2013.01)

(58) Field of Classification Search
CPC ...... A61K 9/0014; A61K 31/277; A61K 9/06; A61K 45/06
See application file for complete search history.

(56) References Cited

U.S. PATENT DOCUMENTS 10,251,871 B2 * 4/2019 Mehrara .............. A61K 31/277

FOREIGN PATENT DOCUMENTS

| CN | 108324687 A * | 7/2018 | ............ A61K 31/277 |
|---|---|---|---|
| WO | WO-2012052180 A1 * | 4/2012 | ............. A61K 31/42 |
| WO | WO 2016189406 A1 | 12/2016 | |
| WO | WO 2017037645 A1 | 3/2017 | |
| WO | WO 2017125841 A1 | 7/2017 | |
| WO | WO-2017168433 A1 * | 10/2017 | ......... A61K 31/4035 |

OTHER PUBLICATIONS

English language machine-translation of CN-108324687-A (published published Jul. 27, 2018); translated Jan. 23, 2024. (Year: 2018).*
Cao, Y.; et al. "Development and Evaluation of a Water-in-oil Microemulsion Formulation for the Transdermal Drug Delivery of Teriflunomide (A771726)" 2019, Chem. Pharm. Bull., vol. 67, pp. 786-794. (Year: 2019).*
Zhang, M.; et al. "The Active Metabolite of Leflunomide A771726 Inhibits Corneal Neovascularization" 2008, Journal of Huazhong University Science and Technology, vol. 28, pp. 364-368. (Year: 2008).*
Zewail, M.; et al. "Hyaluronic acid coated teriflunomide (A771726) loaded lipid carriers for the oral management of rheumatoid arthritis" 2022, International Journal of Pharmaceutics, vol. 623, No. 121939. (Year: 2022).*
PubChem entry—Teriflunomide (PubChem CID 54684141); accessed Jan. 23, 2024. (Year: 2024).*
Xi, H.; et al. "Intra-articular drug delivery from an optimized topical patch containing teriflunomide and lornoxicam for rheumatoid arthritis treatment: Does the topical patch really enhance a local treatment?" 2013, Journal of Controlled Release, vol. 169, pp. 73-81. (Year: 2013).*
Siafaka, P. I.; et al. "Novel electrospun nanofibrous matrices prepared frompoly(lactic acid)/poly(butylene adipate) blends for controlled release formulations of an anti-rheumatoid agent" 2016, European Journal of Pharmaceutical Sciences, vol. 88, pp. 12-25. (Year: 2016).*
Bae, J.; Park, J. W. "Topical delivery of leflunomide for rheumatoid arthritis treatment: evaluation of local tissue deposition of teriflunomide and its antiinflammatory effects in an arthritis rat model" 2016, Drug Development and Industrial Pharmacy, vol. 42, pp. 254-262. (Year: 2016).*
Garzón, L. C.; et al. "Temperature Dependence of Solubility for Ibuprofen in Some Organic and Aqueous Solvents" 2004, Journal of Solution Chemistry, vol. 33, 1379-1395. (Year: 2004).*
Angelova-Fischer, I; et al. "Accelerated barrier recovery and enhancement of the barrier integrity and properties by topical application of a pH 4 vs. a pH 5.8 water-in-oil emulsion in aged skin" 2018, British Journal of Dermatology, vol. 179, pp. 471-477 ( Year: 2018).*

(Continued)

*Primary Examiner* — Eric Olson
*Assistant Examiner* — Benjamin M Brandsen
(74) *Attorney, Agent, or Firm* — Dority & Manning, P.A.

(57) ABSTRACT

The present invention relates to a novel topical pharmaceutical composition of Teriflunomide, comprising teriflunomide or its pharmaceutically acceptable salt in combination with pharmaceutically acceptable excipients, wherein the said composition is effective for use in treatment of pain associated with disorders like inflammation and arthritis. The composition is also useful for relieving the symptoms of pain and arthritis in subjects suffering from autoimmune diseases like multiple sclerosis or rheumatoid arthritis. The said topical composition of teriflunomide is prepared in the form of topical gel, topical cream, topical ointment, topical solution, lotion or topical spray with significantly enhanced permeability and diffusion rate of the drug.

19 Claims, 2 Drawing Sheets

(56) References Cited

OTHER PUBLICATIONS

Pubmed Entry for Angelova-Fischer, I; et al.—shows online publication date as May 28, 2018. (Year: 2018).*

Špiclin, P.; et al. "Sodium ascorbyl phosphate in topical microemulsions" 2003, International Journal of Pharmaceutics, vol. 256, pp. 65-73. (Year: 2003).*

Black, S.; Muller, F. "On the Effect of Temperature on Aqueous Solubility of Organic Solids" 2010, Organic Process Research and Development, vol. 14, pp. 661-665. (Year: 2010).*

Berg, J.; et al. "The analgesic NSAID lornoxicam inhibits cyclooxygenase (COX)-1/-2, inducible nitric oxide synthase (iNOS), and the formation of interleukin (IL)-6 in vitro" 1999, Inflammation Research, vol. 48, 369-379. (Year: 1999).*

Searles, G. E.; et al. "Excipients in topical corticosteroid preparations in Canada" 1989, Canadian Medical Association Journal, vol. 141, pp. 399-405. (Year: 1989).*

Mauro, T.; et al. "Barrier recovery is impeded at neutral pH, independent of ionic effects: implications for extracellular lipid processing" 1998, Archives of Dermatological Research, vol. 290, pp. 215-222. (Year: 1998).*

Aquaphor Original Ointment label, updated Oct. 2017; accessed Aug. 26, 2024. URL: https://dailymed.nlm.nih.gov/dailymed/archives/fdaDrugInfo.cfm?archiveid=284180 (Year: 2017).*

International Search Report mailed on Feb. 19, 2020, in the PCT Application No. PCT/IN2019/050818.

Written Opinion mailed on Feb. 19, 2020, in the PCT Application No. PCT/IN2019/050818.

* cited by examiner

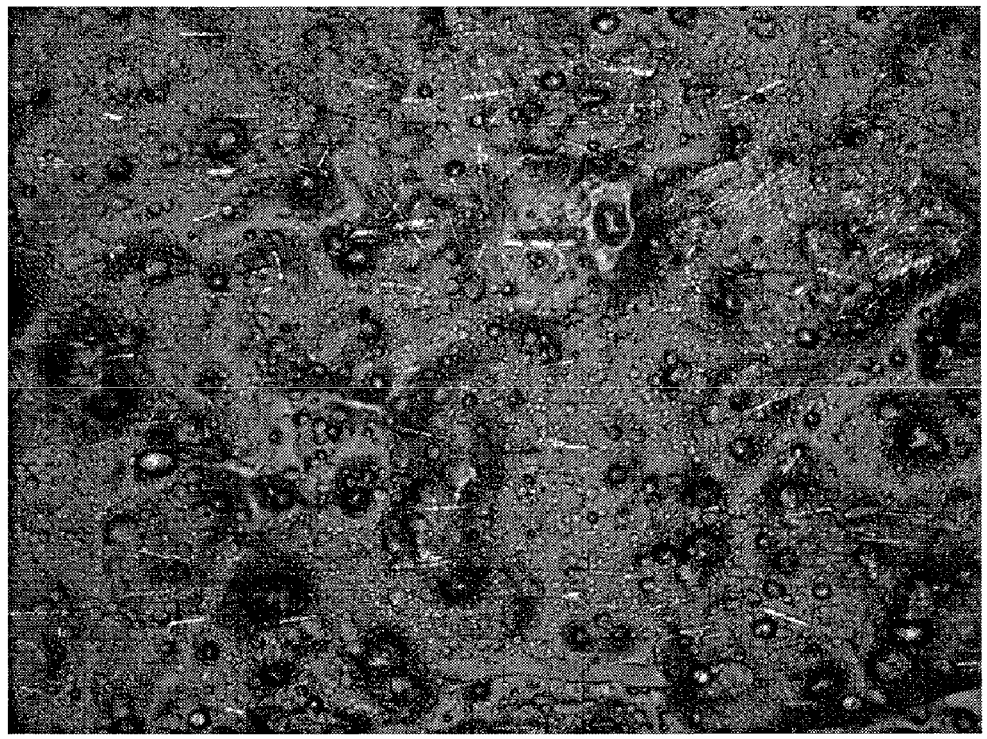
FIGURE 1: PLM images of Teriflunomide Topical Cream at pH 3.1.
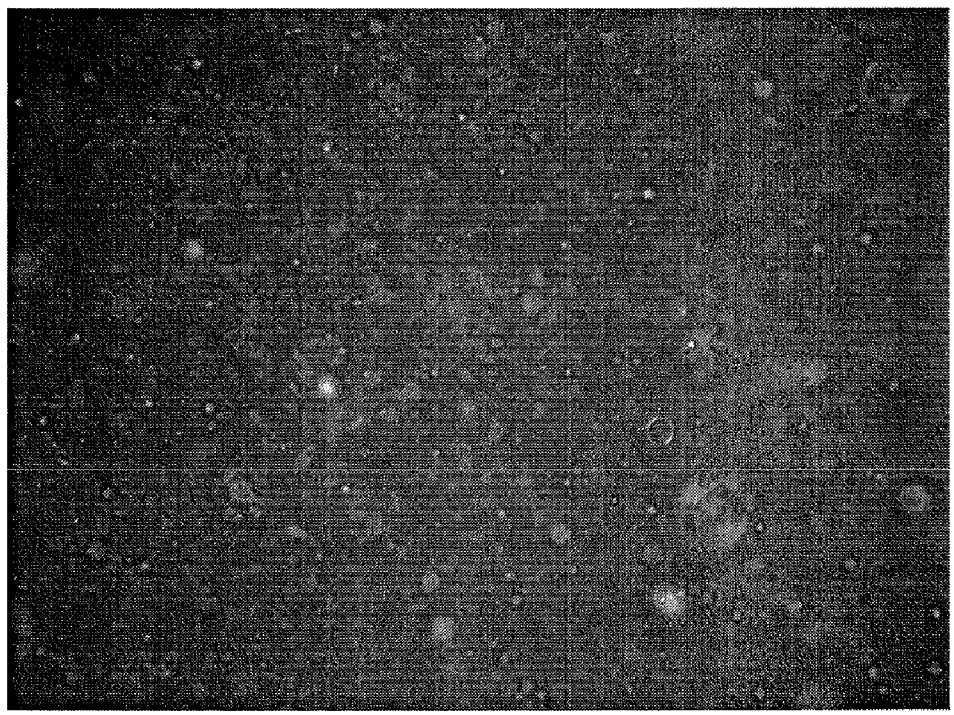
FIGURE 2: PLM images of Teriflunomide Topical Cream at pH 6.8.

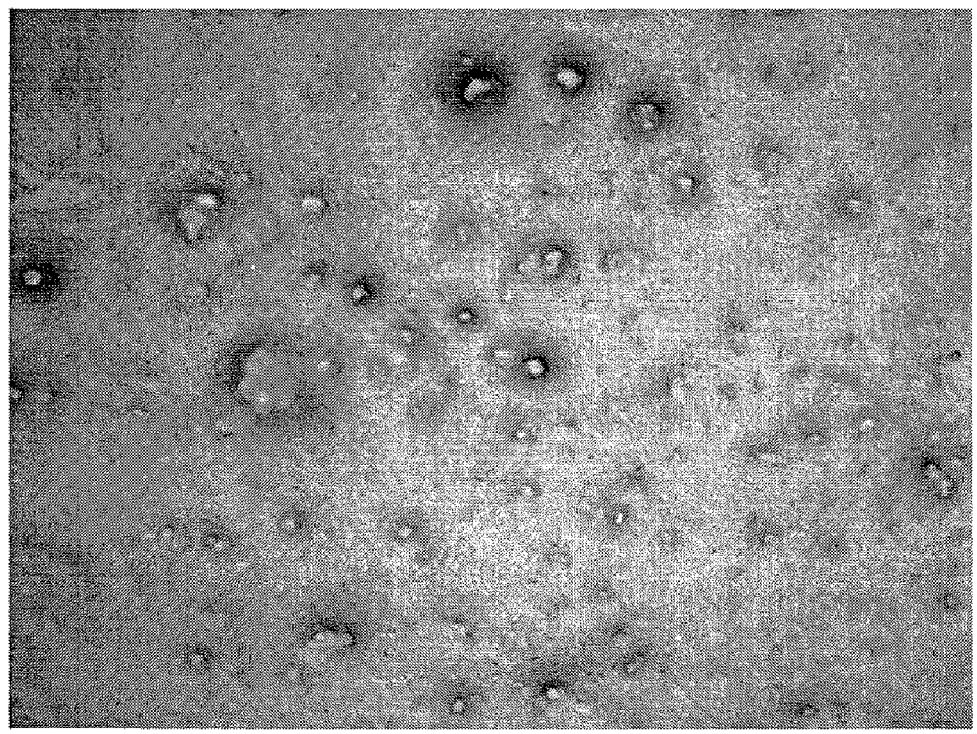
FIGURE 3: PLM images of Teriflunomide Topical gel at pH 6.3.
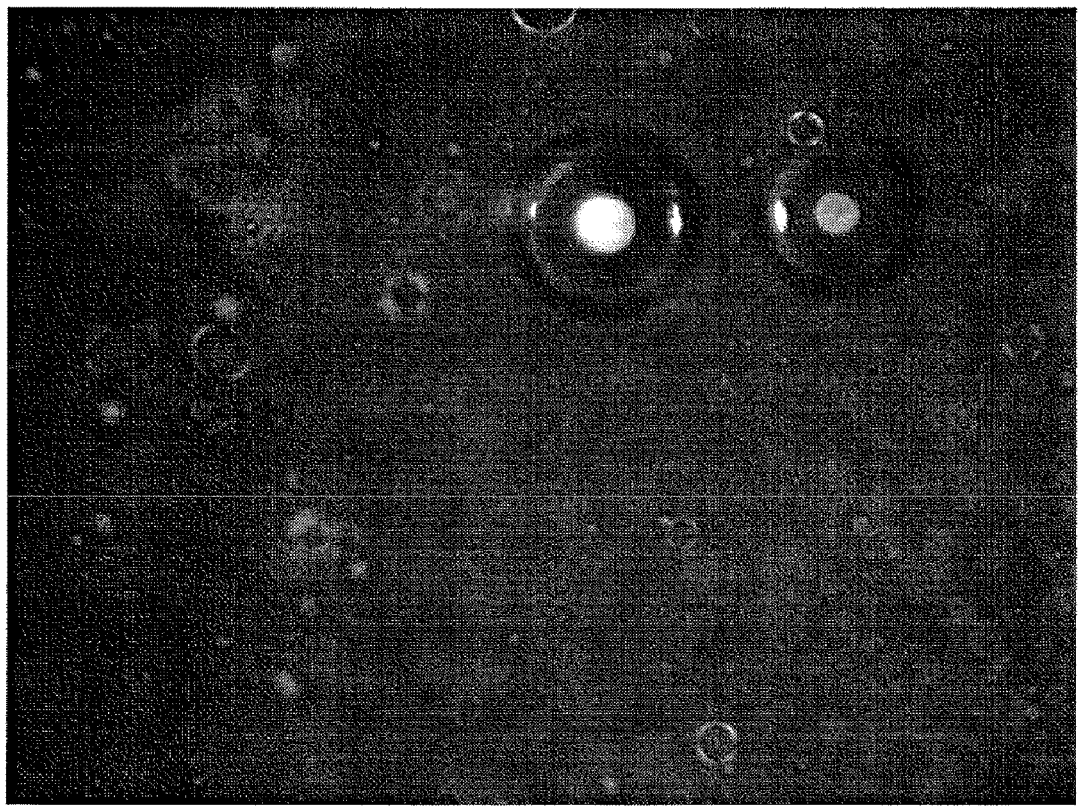
FIGURE 4: PLM images of Teriflunomide Topical Lotion at pH 6.8.

TERIFLUNOMIDE TOPICAL PHARMACEUTICAL COMPOSITIONS

CROSS REFERENCE TO RELATED APPLICATIONS

This application is a § 371 national stage application of International Application No. PCT/IN2019/050818, filed Nov. 5, 2019, which claims priority from Indian Patent Application No. 201841041818 filed on Nov. 5, 2018.

FIELD OF INVENTION

The present invention relates to a novel topical pharmaceutical composition comprising of Teriflunomide or its pharmaceutically acceptable salt with at least one excipient, methods of preparing such compositions for relieving the symptoms of pain, inflammation and arthritis in subjects suffering from various inflammatory diseases like multiple sclerosis or rheumatoid arthritis.

BACKGROUND

Teriflunomide is the active metabolite of leflunomide. It was approved by the FDA as oral tablet dosage form on Sep. 12, 2012 and in the European Union on Aug. 26, 2013 for treatment of patients with relapsing forms of multiple sclerosis.

Teriflunomide is chemically known as (Z)-2-cyano-3-hydroxy-but-2-enoic acid-(4'-trifluoromethylphenyl)-amide, its molecular formula is $C_{12}H_9F_3N_2O_2$, molecular weight is 270.21, melting point is 230° C.~233° C., pKa is 5.2, is weakly acidic, very slightly soluble in water, oil-water partition coefficient is 2.51 and it has the structure as shown in Formula Formula-I

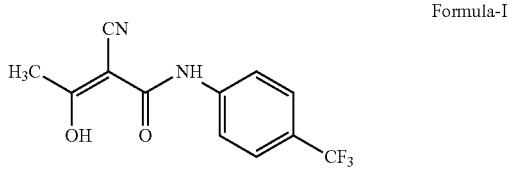 [SMILES: C/C(O)=C(\C#N)C(=O)Nc1ccc(C(F)(F)F)cc1]

Teriflunomide is an active metabolite of leflunomide in DMARDs. It is an immunomodulatory drug with anti-inflammatory effects.

The immunomodulatory mechanisms of Teriflunomide are: It blocks de novo synthesis of pyrimidine nucleotides by selectively reversibly inhibiting dihydroorotate dehydrogenase (DHODH). T-lymphocyte and B-lymphocyte proliferation is inhibited by inhibiting DHODH and reducing DNA synthesis. Lymphocytes that divide slowly or dormant are not affected by TEF and thus do not affect the immune system's response to infection.

Cherwinski H M et al., published in J Pharmacol. Exp. Ther. 1995; 275:1043-1049; reports that the pyrimidines are involved in other cellular functions in addition to DNA/RNA synthesis, including protein and lipid glycosylation, phospholipid synthesis, and DNA repair, which lead to a variety of downstream immunomodulatory effects. However, teriflunomide is a cytostatic rather than cytotoxic drug, as homeostatic hematopoietic cell lines are not affected by DHODH inhibition due to a DHODH-independent "salvage pathway" that can generate necessary cellular pools of pyrimidine.

Further Teriflunomide acts on inflammation mainly by reducing the activity of proliferating T-lymphocytes and B-lymphocytes, thereby diminishing the overall inflammatory response. However the approved compositions of teriflunomide are for oral administration and are for treatment of Multiple Sclerosis.

Teriflunomide is disclosed in U.S. Pat. No. 4,965,276 for the treatment of reactions "graft versus host". U.S. Pat. Nos. 5,459,163 and 5,679,709 disclose compositions of teriflunomide, used to treat autoimmune diseases, in particular lupus erythematosus. U.S. Pat. No. 6,794,410 discloses the use of teriflunomide for treatment of symptoms of multiple Sclerosis.

Publication numbers US 2012/0172427 A1 and WO 2017/037645 A1 disclose solid oral dosage forms of teriflunomide.

U.S. Pat. No. 8,802,735 disclose solid pharmaceutical compositions comprising (Z)-2-cyano-3-hydroxy-but-2-enoic-acid-(4'-trifluoromethylphenyl)-amide, as well as a process for the preparation thereof.

Thus, there is a plethora of literature on solid oral dosage forms of teriflunomide; however, it is a well-known fact that, solid dosage forms have various shortcomings due to systemic absorption, ranging from nausea and diarrhoea to more serious side effects like damage to the hepatic system.

Kappos L. Published in ECTRIMS. Lyon, France; 2012, in a study reported that the adverse effects exhibited in patients treated with teriflunomide are dose-dependent and includes nausea, diarrhoea, hair thinning/decreased hair density, and elevated alanine aminotransferase (ALT) levels. O'Connor P W, et al. 2006; 66:894-900, disclosed that in case of female patients who become pregnant while on teriflunomide should undergo a cholestyramine or activated charcoal-based washout procedure after treatment discontinuation, and confirm that the plasma level is <0.02 g/L.

Therefore a possible alternative to oral therapy, to avoid such systemic toxicity issues, is the development of topical compositions. The delivery of active agents across the skin or mucosal membrane is convenient, pain-free, non-invasive and circumvents problems associated with the "first pass effect". Such topical drug delivery is typically restricted to specific drugs with specific lipophilic/hydrophilic balance and ability to penetrate the stratum corneum.

There are few literature discussed below which disclose various topical compositions.

US publication no. 2018/0028514 A1, discloses pharmaceutical compositions and methods of treating or preventing edema, using an anti-T cell agent, an anti-TGF-B agent, or an anti-angiotensin agent, preferably a combination of at least two such agents. The pharmaceutical compositions can be formulated for systemic or local administration.

Bae J et al., Drug Dev. Ind. Pharm. 2016; 42(2):254-62, investigated whether leflunomide can be delivered topically and metabolized into teriflunomide through the skin, and evaluated the therapeutic effect of topical leflunomide.

PCT publication no. WO 2012/052180 A1, discloses a combination comprising (a) DHODH inhibitors and (b) COX inhibitors and their treating skin diseases or disorders are disclosed.

PCT publication no. WO 2015/100365 A1, discloses a method of treating a subject afflicted with multiple sclerosis (MS) or presenting a clinically isolated syndrome (CIS) comprising administering to the subject laquinimod as an add-on therapy to or in combination with a greater than minimal effective dose of teriflunomide.

All the above discussed prior art either disclose solid dosage forms for oral administration or various combination dosage forms for topical application. Further as already discussed the side effects of oral therapy like diarrhoea, headache, nausea, vomiting, are well known.

Thus systemic absorption of oral dosage forms creates certain disadvantages which require further concern.

The applicant in the present application has explored the anti-inflammatory and pain relief property of teriflunomide. As it is well known that today, pain has become a universal disorder with serious and costly public health issues, and a challenge for almost all age groups. In general, there are two basic types of pain: acute and chronic. Acute pain, for the most part, results from disease, inflammation, or injury to tissues. This type of pain generally comes on suddenly, for example, after trauma or surgery. In some instances, it can become chronic. Chronic pain is widely believed to represent disease itself. Chronic pain persists over a longer period of time than acute pain and is resistant to most medical treatments. It can, and often does, cause severe problems for patients.

In the past, corticosteroids were the most important for the topical treatment of inflammatory diseases. Usually weak to moderately strong corticosteroids for treating inflammatory, allergic, and pruritic skin diseases were used. Although short-term treatment (a few days or weeks) with oral steroids is relatively safe, long-term treatment (more than 3 months) can cause undesirable side effects, including Coriolus syndrome, thinning of the skin, and the sensitivity of infection is elevated.

Non-narcotics and non-steroidal drugs are also commonly used in medical practice, but they still do not simultaneously fight inflammation and pain. These drugs are salicylates and other drugs commonly referred to as non-steroidal anti-inflammatory drugs (NSAIDs).

Further in inflammatory disorders for example in rheumatoid Arthritis, the inflammatory relief can be given by NSAIDs. However, most of the adverse effects of non-steroidal anti-inflammatory drugs are gastrointestinal irritation, and long-term administration increases the risk of gastrointestinal adverse events. NSAID can cause stomach ulcers and bleeding if used for long periods of time. Topical delivery is desirable route of administration to meet the local therapeutic needs of pain, and inflammatory disorders like rheumatoid arthritis and to overcome the above-mentioned adverse reactions of NSAIDs. Unfortunately, NSAIDs are often not fully absorbed when administered topically.

The present inventors have developed a very stable and effective topical composition of teriflunomide which relieves the painful symptoms in inflammatory diseases like rheumatoid arthritis, systemic lupus erythematosus, psoriatic arthritis and fibromyalgia etc., with or without the NSAIDs.

However, teriflunomide is a weakly acidic drug with poor percutaneous permeability, limiting their transdermal delivery applications and getting a stable and non-precipitating composition is a challenging prospect.

Further, teriflunomide is difficult to formulate as topical composition due to its solubility issues and complexity associated with its precipitation and stabilization. Inventors of the present application have been involved in the research and development of pharmaceutical formulations, and through extensive research have developed a stable, compliant and effective topical composition of teriflunomide.

SUMMARY OF THE INVENTION

The present invention relates to a topical teriflunomide composition for alleviating the symptoms of related to inflammatory diseases like rheumatoid arthritis, psoriasis, arthritic pain and multiple sclerosis.

A further object of the present invention is to provide a topical pharmaceutical composition suitable for topical application, comprising teriflunomide or its pharmaceutically acceptable salt in combination with pharmaceutically acceptable excipients, which is effective in treatment of pain associated with disorders like inflammation and arthritis.

In a further object the present invention provides topical pharmaceutical compositions of teriflunomide which is stable for a longer storage period and does not contain any known impurity initially and on storage the total impurity is controlled within the acceptable limits as per regulatory requirements.

In a further object the present invention provides teriflunomide pharmaceutical compositions in the form of topical gel, topical cream, topical ointment, topical solution, lotion or topical spray.

Another object of the invention is to provide a topical composition for effectively relieving the symptoms of inflammatory pain and free from hepatic toxicity issues of conventional formulations.

In another object, the present invention provides the topical pharmaceutical composition of teriflunomide with enhanced permeability and diffusion rate.

In another object, the composition comprises suitable oil vehicle and emulsifier in association with thickener and a permeation enhancer which in combination imparts enhanced diffusion of the drug into the skin layers.

In another object the present invention provides the topical pharmaceutical composition with excipients to impart better feel to the skin by giving a composition free of gritty particles and greasiness, and thus causing lower irritation to the skin.

In yet another object the topical pharmaceutical compositions according to the present invention may further comprise of one or more active ingredients selected from the group consisting of: COX inhibitors; Corticosteroids; Immuno-supressants; Counter-irritants; and Antihistaminic agents.

BRIEF DESCRIPTION OF DRAWINGS

FIG. 1: Polarizing light microscopy (PLM) images of Teriflunomide Topical Cream at pH 3.1.

FIG. 2: Polarizing light microscopy (PLM) images of Teriflunomide Topical Cream at pH 6.8.

FIG. 3: Polarizing light microscopy (PLM) images of Teriflunomide Topical gel at pH 6.3.

FIG. 4: Polarizing light microscopy (PLM) images of Teriflunomide Topical Lotion at pH 6.8.

DETAILED DESCRIPTION

The present invention relates to stable and non-precipitating topical compositions of teriflunomide for relieving the symptoms of inflammation, arthritic pain and rheumatoid arthritis.

The present invention also provides a topical pharmaceutical composition suitable for topical application, comprising teriflunomide or its pharmaceutically acceptable salt in combination with pharmaceutically acceptable excipients, which is effective in treatment of pain associated with disorders like inflammation and arthritis.

It has been found that pharmaceutical compositions in the form of topical formulations of teriflunomide as prepared provide desired pharmacological actions and fewer side effects.

It has been found that pharmaceutical compositions in the form of topical formulations of teriflunomide as prepared are stable for a longer storage period.

In one embodiment of the present invention, teriflunomide is provided in the pharmaceutical compositions in the form of topical gel, topical cream, topical ointment, topical solution or topical spray.

In yet another preferred embodiment of the present invention the topical composition of the present invention is effective for inflammation mediated pain irrespective of the disorder.

In yet another embodiment of the invention, the topical composition of the present invention is effective for relieving the symptoms of inflammatory pain and free from hepatic toxicity issues of conventional formulations.

In another embodiment of the present invention, teriflunomide is provided in the pharmaceutical composition in the form of topical gel or cream or ointment or solution or spray along with suitable solvent and carrier.

In another preferred embodiment, the inventors of the present invention have developed the topical pharmaceutical composition of teriflunomide with enhanced permeability and diffusion rate.

In another preferred embodiment of the present invention, the composition comprises suitable oil vehicle and emulsifier in association with thickener and a permeation enhancer. The inventors have surprisingly found that such combination imparts enhanced diffusion of the drug into the skin layers.

In another embodiment of the present invention, topical gel or cream or ointment or solution or spray comprises excipients that are hydrophilic or lipophobic in nature.

In another embodiment of the present invention, topical gel or cream or ointment or solution or spray comprises excipients that are hydrophobic or lipophilic in nature.

In most preferred embodiment of the present invention, the topical composition of the invention comprises amphiphilic or non-ionic surfactants as excipients.

In another preferred embodiment, a solvent/co-solvent system along with suitable emulsifiers or amphiphilic/non-ionic surfactants was used to achieve enhanced solubility of the drug.

In another embodiment of the present invention, the topical pharmaceutical composition comprises excipients to provide better feel to the skin by giving a composition free of gritty particles and greasiness, and thus causing lower irritation to the skin.

In yet another embodiment of the present invention, topical pharmaceutical composition comprises excipients to provide better feel to the skin, lower irritation and low or non-staining to the skin or the clothes.

In one of the embodiment of the present invention, the topical pharmaceutical compositions may optionally comprise of fragrance.

In another embodiment of the present invention, topical composition is an amphiphilic cream or lipid nano emulsion cream or a nano emulsion cream.

In one embodiment, the invention is directed to a topical composition for treating arthritic pain comprising a therapeutically effective amount of teriflunomide and a pharmaceutically acceptable carrier.

The topical pharmaceutical compositions according to the present invention may further comprise of one or more active ingredients selected from the group consisting of:
a) COX inhibitors;
b) Corticosteroids;
c) Immuno-supressants;
d) Counter-irritants; and
e) Antihistaminic agents.

In another preferred embodiment of the present invention, the teriflunomide of the topical composition can be combined with one or more active ingredient selected from a COX inhibitor or counter-irritant.

The combination compositions of the present invention provide various advantages like better and improved patient compliance, synergist effect, enhanced efficacy, reduced side effects and overall economic advantage.

In yet another embodiment the topical compositions of the present invention contain one or more buffering or pH modifying agent to adjust the pH of the composition. Useful pH modifiers include, but are not limited to, an alkali metal hydroxide such as, for example, sodium hydroxide, potassium hydroxide, ammonium hydroxide and the like and mixtures thereof. In one embodiment the neutralizer is sodium hydroxide.

In another preferred embodiment the process for preparation of the topical composition imparts an important stability character to the composition, wherein the process comprises:
i. Adding the drug to a mixture of oil-solvent or co-solvent with a permeation enhancer or solubilizer and heating;
ii. After the complete solubilization of the API, a suitable pH adjusting agent is added with stirring;
iii. Followed by addition of optional preservatives;
iv. Then to the above mixture suitable emulsifiers were added and mixed to dissolve followed by cooling;
v. Then a solution or dispersion of thickening agent is added to the above mixture and mixed, followed by cooling to get the desired formulation.

A "therapeutically effective amount" is an amount necessary to palliate at least one symptom of arthritis. For example, a therapeutically effective amount is sufficient to treat (i.e. alleviate or reduce) at least one of: pain, redness, inflammation, cracking, scaling, etc. Preferably, the therapeutically effective amount of teriflunomide comprises between 0.5 to 10% by weight of the composition, more preferably 0.5 to 5%.

The term "pharmaceutically acceptable" means approved by a regulatory agency of the Federal or state government or listed in the U.S. Pharmacopeia or other generally recognized pharmacopeia for use in animals, and more particularly in humans.

The term "carrier" refers to a diluent, adjuvant, excipient, penetration enhancer, solubilizer or vehicle with which an active ingredient is administered. Such pharmaceutical carriers can be liquids, such as water and oils, including those of petroleum, animal, vegetable or synthetic origin. Preferably, the pharmaceutically acceptable carrier comprises excipients commonly used in topically applied formulations (water, oil-based lotions, sprays, ointments, gels etc.).

In an embodiment of the present invention, the topical composition has excipients that help deep penetration of teriflunomide into the skin and provide ease of application, spreadability and cleaning.

Topical pharmaceutical compositions of the present invention may be, but not limited to, a cream, ointment, gel, solution or spray.

In a preferred embodiment the topical pharmaceutical compositions of the invention includes teriflunomide in the concentration of 0.5% to 10% by weight.

In another preferred embodiment the topical pharmaceutical compositions of the invention include teriflunomide and carrier or permeation enhancer in the ratio of 1:1 to 1:50 or 1:1 to 1:20 or 1:1 to 1:10.

In another preferred embodiment the topical pharmaceutical compositions of the invention include teriflunomide and solvent or co-solvent in the ratio of 1:1 to 1:50 or 1:1 to 1:20 or 1:1 to 1:10.

In another embodiment the topical pharmaceutical compositions of the invention include thickener in the weight percentage of 0.1-8% w/w.

Topical pharmaceutical compositions of the invention have a pH in the physiological range between 3 to 8 or 4.5 to 7.5.

In another exemplary embodiment the topical composition of the invention comprises teriflunomide 0.5-10%, solvent 5-40%, optional co-solvent 5-40%, emulsifier 2-20%, optional co-emulsifier 2-20%, permeation enhancer/solubilizer 2-45%, preservatives 0.01-6.0%, thickener 0.1-5.0%, pH modifier or buffering agent 0.5-10%, diluent 20-80%.

In another preferred embodiment in the process for preparation of the topical composition the addition step of alkali or base to adjust the pH of the composition plays crucial role in the stabilisation of final composition.

In yet another preferred embodiment, the pH of the composition is adjusted immediately after the solubilisation step in order to maintain the integrity of the topical composition and to prevent precipitation of the active ingredient or components. Further the pH is adjusted by adding the alkali solution under stirring, only after complete solubilization of the API.

Non-limiting lists of the excipients that can be used in the composition are:

A pharmaceutically acceptable carrier may comprise water, glycerin, petrolatum, stearic acid, glycol stearate, dimethicone, isopropyl isostearate, tapioca starch, cetyl alcohol, glyceryl stearate, magnesium aluminum silicate, carbomer, ethylene brassylate, triethanolamine, disodium EDTA, phenoxyethanol, methyl paraben, propyl paraben, ethanol, bio-polymers (e.g., sodium hyaloronate), liposomes, nano- and micro-particulate carriers, and/or titanium dioxide. More preferably, the pharmaceutically acceptable carrier comprises dimethyl sulfoxide (DMSO), glycerol, propylene glycol, petrolatum water, and one or more pharmaceutically acceptable penetration enhancer (absorption promoter and/or accelerants).

Typically, the topical compositions of the invention comprise skin penetration enhancers, pharmaceutical surfactants and solubility enhancers, oil phase components, aqueous phase components, emulsifiers, moisturizers, antioxidants, vitamins, lubricants, preservatives, stabilizers and other ingredients.

Skin penetration enhancers reversibly decrease the barrier resistance of the skin, which increases the amount of teriflunomide absorbed. Preferably, skin penetration enhancers include, but are not limited to, sulfoxides (e.g. DMSO), azones (e.g. laurocapram), pyrrolidones (e.g., 2-pyrrolidone), alcohols and alkanols (e.g., ethanol, decanol, etc.), oleic acid (and derivatives thereof), glycols (e.g., propylene glycol), dimethylformamide (DMF), dimethylacetamide (DMAC), fatty alcohols (e.g., lauryl alcohol), fatty acid esters, fatty acids, fatty alcohol ethers (e.g., EO-2-oleyl ether), terpenes, and biologics (e.g., lecithin).

Pharmaceutical surfactants or solubility enhancers include, but are not limited to, lauryl alcohol, polyoxyethylene ether, polyoxyethylene glycerol monostearate, stearic acid ester oxygen poly hydrocarbon, vitamin E succinate polyethylene glycol ester, sorbitan esters, polyoxyethylene castor oil, polyoxyethylene hydrogenated castor oil, poloxamer, organic esters (e.g. ethylene acetate), and poly hill dinitrate 80 (i.e. Tween 80 or its mixture). In a preferred embodiment, the pharmaceutical surfactants or solubility enhancers include DMSO, polyvinylpyrrolidones, stearic acid hydrocarbon oxygen Poly (40) ester, lauryl alcohol polyoxyethylene (23) ether, vitamin E succinate polyethylene glycol ester, ethylene acetate, and polyoxyethylene (40) hydrogenated castor oil (and its mixtures, i.e. polyoxy (40) stearate). Still, in a more preferred embodiment the pharmaceutical surfactants or solubility enhancers include sodium lauryl sulphate and sorbitan esters.

Suitable oily phase may include, but are not limited to, glyceryl monoacetate, glycerol diacetate, glyceryl triacetate, stearic acid, soybean oil, corn oil, peanut oil, palmitic acid, palm oil, sunflower oil, olive oil, coconut oil, sesame oil, cotton seed oil, rapeseed oil, oleic acid, medium-chain triglycerides, single-decane triglyceride, animal fat (e.g., lanolin), mineral oils, paraffin, beeswax, petrolatum, hydrocarbons, vaseline, and mixtures thereof.

Aqueous phase components include, but are not limited to, de-ionized water, glycerol gelatin, cellulose derivatives (e.g., microcrystalline cellulose (Avicel PH 101)), and polyethylene glycol (PEG 300 to PEG 6000), and mixtures thereof.

Emulsifiers or co-emulsifiers include, but are not limited to oleyl alcohol, polyoxyethylene oleyl ether, PEG-40 stearate, ceteareth-12, ceteareth-20, ceteareth-30, glyceryl stearate, PEG-100 stearate, methyl myristate, isopropyl myristate, Arlacel 165, glyceryl stearate, PEG-100 stearate, steareth-2 and steareth-20, dimethicone copolyol, Polysorbate 20 (Tween 20), cetyl esters wax, Polysorbate 40 (Tween 40), Polysorbate 60 (Tween 60), Polysorbate 80 (Tween 80), Emulcire, Gelot, lauramide DEA, cocamide DEA, and cocamide MEA, Phospholipid PTC, alginate, carrageenan, Glucate DO, methylcellulose, polyvinyl alcohol, Carbopol and Carbomer. Preferably, emulsifiers are selected from the group consisting of cetostearyl alcohol, stearic acid, magnesium stearate, sodium lauryl sulfate, triethanolamine, and magnesium aluminum silicate.

Moisturizers include, but are not limited to, glycerol, propylene glycol, and sorbitol.

Antioxidants include, but are not limited to, water soluble antioxidants, lipid-soluble antioxidants, vitamin C, vitamin C palmitate, propyl gallate, vitamin E (tocopherol), tert-butyl ether-hydroxybenzoate fennel, 2,6 di-tert-butyl-p-cresol, BHA, BHT, or mixtures of one or more antioxidants.

Lubricants include, but are not limited to, urea, magnesium stearate, sodium lauryl sulfate, polyethylene glycol, and silica gel powder.

Preservatives include, but are not limited to, chloro-m-cresol, citric acid, disodium edetate, ethoxylated alcohol, glycerin, 1,2,6-hexanetriol, methylparaben, parabens, potassium, sorbate, propyl gallate, propylene glycol, propyl paraben, sodium bisulfate, sodium citrate, butyl paraben, sodium metabisulfite, chlorocresol, sorbic acid, tannic acid, zinc stearate, butylated hydroxytoluene, butylated hydroxyanisole, benzoic acid, salicylic acid, propyl paraben, dichlorobenzyl alcohol, formaldehyde, alpha-tocopherol, sodium ascorbate, ascorbic acid, ascorbyl palmitate phenol, m-cresol, bisphenol, cetrimide, benzalkonium chloride, sorbic acid, phenoxyethanol, and benzoyl peroxide. Preferably, preservatives are selected from the group consisting of hydroxylethyl benzene, hydroxylmethyl benzene, phenoxyethanol, chlorocresol, propyl paraben, and methyl paraben.

Some of the critical excipients where the solubility of teriflunomide was evaluated during pre-formulation stage includes, but are not limited to, Sunflower oil & Hydrogenated vegetable oil by AKK Kamani used as Oil Vehicle;

Labrifil M 1944 CS & Capryol 90 used as Non-ionic surfactant; Transcutol P used as solvent (solubilizer or permeation enhancer); Emulcire 61 WL 2659 used as emulsifier; Labrifil M 2130 CS used as non-ionic water dispersible surfactant; Gelot 64 used as non-ionic oil/water emulsifier; DMSO, IPA, PG used as solvent; Poly-oxyl 35 Castor Oil (Kolliphore EL) by BASF & Tween 80 used as Non-ionic surfactant; Kolli solve (MCT) as emolinet, Kolli solve (GTA) as solvent solubilizer, Kolli cream (OA) as emolinet oil or solubilizer or permeation enhancer, Kolli cream (3C) as polar oil, Kolli cream (IPM) as skin penetration enhancer, Kolli cream (DO) as solubilizer or penetration enhancer; Coconut oil by Parachut, Labrafac PG (70-90° C.), Labrafac Liphophile WL 1349 (70-90° C.), Maisine CC (70-90° C.), Peceol (70-90° C.) as oil vehicle; 1-methyl-2-pyrrolidone as Solvent; Labrafil-M-2125 (70-90° C.) as non-ionic water dispersible surfactant; Labrasol as Solvent.

In an embodiment of the invention, topical composition of present invention has excipients that help in adjusting the pH of the composition. The pH of the topical compositions may be adjusted between from about 4 to about 8 to provide a non-irritating and non-precipitating composition. Such agents include many pharmaceutically acceptable acids, bases and buffers. Suitable acids may include one or more of hydrochloric acid, phosphoric acid and lactic acid. Suitable bases may include one or more of diethanolamine, triethanolamine and sodium hydroxide. Suitable buffers may include phosphates, such as monobasic sodium phosphate, dibasic sodium phosphate, lactates and citrates.

"Excipient" means any substance that is combined with a drug to produce a pharmaceutical dosage form. Such excipients can be combined to produce the desired skin feel or to facilitate drug delivery. Non-limiting examples of excipients include, for example, water, thickeners, wetting agents, emollients, surfactants, preservatives, oils, colorants, antioxidants, fragrances, mineral oils, liquid paraffin, and white petrolatum. The excipients can also have single or multiple functions within the embodiment.

Each excipient may be used for one or multiple functional attributes like as solvent, emulsifier, permeation enhancer, solubilizer, preservative, thickener, and diluent.

"Topical dose" refers to the amount or concentration of a drug that reaches a local target and exhibits a desired therapeutic effect.

By "local inflammatory condition" is meant a condition in which an inflammatory process is an element of a local target condition. Examples of topical inflammatory conditions contemplated herein include any of the following conditions: pain, swelling, edema, redness, tissue damage, attack on the skin, cellular injury, and the like.

"Local target" refers to a tissue affected by a condition that can be treated by the delivery of a drug, such as skin, joints, muscles, and ligaments, with the compositions of the present invention.

"%" as used in connection with the concentration of the components of the composition means the ratio of the weight of the component expressed as a percentage to the total weight unless otherwise stated.

"Therapeutically effective" or "treatment" when referring to a formulation means that when applied to the skin according to sound medical practice, it produces a significant effect in order to reduce or prevent a local inflammatory response. This significant effect can be a general pathological level (eg, swelling, redness, or a visible reduction in any characteristic cutaneous pathology. Therapeutic effective or therapeutic can be curative, palliative and/or disease resistant or prophylactic. This is not meant to show a quantitative effect, but rather has a clinically observable beneficial effect.

EXAMPLES

The following examples are set forth to aid in an understanding of the invention, and are not intended, and should not be construed, to limit in any way the invention set forth in the claims that follow thereafter. A person skilled in the art will readily recognize the various modifications and variations that may be performed without altering the scope of the present invention. Such modifications and variations are encompassed within the scope of the invention and the examples do not in any way limit the scope of the invention.

Example 1: Teriflunomide Topical Cream

| Component | % w/w |
|---|---|
| Teriflunomide | 0.5-10.0 |
| Labrafac PG | 5-40 |
| Labrafac Liphophile WL 1349 | 5-40 |
| Emulcire 61 WL 2659 | 2-20 |
| Gelot 64 | 2-20 |
| DMSO | 2-45 |
| Methyl paraben | 0.1-6.0 |
| propyl paraben | 0.01-5.0 |
| Carbopol | 0.1-4.0 |
| 10% NaOH | 0.5-10.0 |
| Purified water | 20-70 |

Brief Manufacturing Process:
1. Teriflunomide was added to a mixture of solvent and/or co-solvent and DMSO. The mixture was heated above 50° C.
2. After complete solubilization of the API, alkaline solution was added under stirring to the step 1 drug solution.
3. Then methyl and/or propyl parabens were added to step 2) resultant mixture.
4. Followed by addition of suitable emulsifier and/or co-emulsifier to the step 3 mixture and solubilising.
5. Then the above mixture was allowed to cool to a temperature of 50-65° C.
6. Separately a solution of a thickening agent in aqueous or alcoholic phase was prepared and allowed to disperse uniformly under stirring.
7. Then the dispersion step 6) was added to the mixture obtained in step 5) drop wise under stirring. Followed by mixing the resultant mixture and allowing cooling to room temperature.

Observations:
i. The resulting teriflunomide cream was found to be of adequate consistency;
ii. The formulation was free of gritty particles and greasiness;
iii. The pH of the formulation was found to be in range of 5-7.5;
iv. The consistency of the formulation did not deteriorate on storage and was found to be sufficiently stable;
v. No crystals were observed under PLM;
vi. The viscosity of the formulation was found to be in range of 600-950 cps.

Example 2: Teriflunomide Topical Cream 2% w/w

| Component | % w/w |
|---|---|
| Teriflunomide | 2.00 |
| Labrafac PG | 10.00 |
| Labrafac Liphophile WL 1349 | 12.00 |
| Emulcire 61 WL 2659 | 9.00 |
| Gelot 64 | 3.60 |
| DMSO | 10.0 |
| Methyl paraben | 0.50 |
| propyl paraben | 0.06 |
| Carbopol | 0.30 |
| 10% NaOH | 4.00 |
| Purified water | 48.54 |

Brief Manufacturing Process:
1. Teriflunomide was added to a mixture of Labrafac PG, Labrafac Liphophile WL 1349 and DMSO. The mixture was heated to 70° C.-85° C.
2. After complete solubilization of the API, 10% NaOH solution was added under stirring to the step 1 drug solution.
3. Then methyl and propyl parabens were added to the resultant mixture of step 2).
4. Followed by addition of Emulcire 61 WL 2659 and Gelot 64 to the step 3 mixture and solubilising.
5. Then the above mixture of step 4) was allowed to cool to a temperature of 60° C.
6. Separately Carbopol was added to purified water and allowed to disperse uniformly under stirring.
7. Then the dispersion obtained in step 6) was added to the mixture of step 5), drop wise under stirring. Followed by mixing the resultant mixture and allowing cooling to the room temperature.

Observations:
i. The resulting teriflunomide cream was found to be of adequate consistency;
ii. The formulation was free of gritty particles and greasiness;
iii. The pH of the formulation was found to be in range of 5.5-7.5;
iv. The consistency of the formulation did not deteriorate on storage and was found to be sufficiently stable;
v. No crystals were observed under PLM;
vi. The viscosity of the formulation was found to be in range of 650-850 cps.

Example 3: Teriflunomide Topical Gel

| Component | % w/w |
|---|---|
| Teriflunomide | 0.5-10% |
| DMSO | 2-45 |
| Tween 80 | 5-50 |
| Span 20 | 5-40 |
| Polyoxyl 35 castor oil | 10-50 |
| Methyl paraben | 0.1-6.0 |
| propyl paraben | 0.01-5.0 |
| Kolli cream 3C | 3-15 |
| Carbopol | 0.1-4.0 |
| Purified water | 20-70 |

Brief Manufacturing Process:
1. A mixture of drug, non-ionic surfactants and emulsifiers were mixed together on magnetic stirrer at a temperature of 70-95° C. The heating and stirring was continued till clear solution was obtained;
2. Followed by adding a permeation enhancer to the step 1 clear solution under stirring.
3. Then purified water was added to the mixture obtained in step 2) under homogenization to form emulsion.
4. Separately a mixture of preservatives was dissolved in DMSO and Carbopol was dispersed in purified water, and then transferred into the preservative solution in DMSO.
5. Followed by stirring.
6. Thereafter Step 3) and step 4) mixtures were mixed under high speed homogenization for 10-20 min.
7. An emulsion was formed and its pH was adjusted to slightly acidic pH with alkaline solution.

Observation
i. The resulting teriflunomide gel was found to be of adequate consistency;
ii. The formulation was free of gritty particles and greasiness;
iii. The pH of the formulation was found to be in range of 5.0-6.5;
iv. No crystals were observed under PLM.

Example 4: Teriflunomide Topical Gel 1% w/w

| Component | % w/w |
|---|---|
| Teriflunomide | 1.00 |
| DMSO | 10.00 |
| Tween 80 | 20.00 |
| Span 20 | 10.00 |
| Polyoxyl 35 castor oil | 30.00 |
| Methyl paraben | 0.50 |
| propyl paraben | 0.05 |
| Kollicream 3C | 5.00 |
| Carbopol | 0.75 |
| Purified water | 48.54 |

Example 5: Teriflunomide Topical Gel 1% w/w

| Component | % w/w |
|---|---|
| Teriflunomide | 1.00 |
| N-Methyl-2-Pyrrolidone | 8.00 |
| Sepineo P600 | 2.00 |
| Isopropyl myristate | 5.00 |
| Absolute ethanol | 5.00 |
| Methyl paraben | 0.50 |
| Propyl paraben | 0.05 |
| Purified Water | 78.45 |

Example 6: Teriflunomide Topical Gel 2% w/w

| Component | % w/w |
|---|---|
| Teriflunomide | 2.00 |
| N-Methyl-2-Pyrrolidone | 17.00 |
| Sepineo P600 | 2.00 |
| Isopropyl myristate | 5.00 |
| Absolute ethanol | 5.00 |
| Methyl paraben | 0.50 |
| Propyl paraben | 0.05 |
| Purified Water | 68.45 |

Observation
i. The resulting teriflunomide gel was found to be of adequate consistency;
ii. The API distribution was uniform throughout the gel;
iii. Drug crystals were observed;
iv. Though the API precipitated, the gel did not have gritty particles and had smooth texture.

Example 7: Teriflunomide Topical Gel 2% w/w

| Component | % w/w |
|---|---|
| Teriflunomide | 2.00 |
| DMSO | 10.00 |
| Maisine CC | 10.00 |
| Tween 80 | 2.00 |
| Methyl paraben | 0.50 |
| Propyl paraben | 0.05 |
| Sepineo P 600 | 2.00 |
| Purified Water | 73.45 |

Observation
i. The resulting teriflunomide gel was found to be of adequate consistency;
ii. The formulation was free of gritty particles and greasiness;
iii. The pH of the formulation was found to be in range of 4.0-5.0.

Example 8

Based on observations of various examples as above, optimized compositions of Teriflunomide using various concentrations of drug were prepared for enhanced diffusion and best topical effect on skin for various inflammatory conditions.

The topical compositions in concentration ranges of 0.5%-10.0% were prepared in evaluated as in below:

Example 8.1: Teriflunomide Topical Creams

| | | Teriflunomide Topical Creams | | | | | |
|---|---|---|---|---|---|---|---|
| S. No | Name of the ingredient | Strength (% w/w) | | | | | |
| | | 0.5% w/w | 1.0% w/w | 2.0% w/w | 4.0% w/w | 6.0% w/w | 10.0% w/w |
| 1 | Teriflunomide | 0.5 | 1 | 2 | 4 | 6 | 10 |
| 2 | Labrafac PG | 10 | 10 | 10 | 10 | 10 | 10 |
| 3 | Labrafac Liphophile WL 1349 | q.s. | q.s. | q.s. | q.s. | q.s. | q.s. |
| 4 | Emulcire 61 WL 2659 | 9 | 9 | 9 | 9 | 9 | 9 |
| 5 | Gelot 64 | 3.6 | 3.6 | 3.6 | 3.6 | 3.6 | 3.6 |
| 6 | DMSO | q.s. | q.s. | q.s. | q.s. | q.s. | q.s. |
| 7 | Methyl paraben | 0.5 | 0.5 | 0.5 | 0.5 | 0.5 | 0.5 |
| 8 | propyl paraben | 0.06 | 0.06 | 0.06 | 0.06 | 0.06 | 0.06 |
| 9 | Carbopol | 0.3 | 0.3 | 0.3 | 0.3 | 0.3 | 0.3 |
| 10 | 10% NaOH Solution | 4 | 4 | 4 | 4 | 4 | 4 |
| 11 | Purified water | q.s. | q.s. | q.s. | q.s. | q.s. | q.s. |
| | Total (%) | 100.00 | 100.00 | 100.00 | 100.00 | 100.00 | 100.00 |

Brief manufacturing process:
1. Teriflunomide was added to a mixture of Labrafac PG, Labrafac Liphophile WL 1349 and DMSO, then the mixture was heated to 70° C.-85° C.
2. After complete solubilization of the API, 10% NaOH solution was added under stirring to the step 1 drug solution.
3. Then methyl and propyl parabens were added to the resultant mixture of step 2).
4. Followed by addition of Emulcire 61 WL 2659 and Gelot 64 to the step 3 mixture and solubilising.
5. Then the above mixture of step 4) was allowed to cool to a temperature of 60° C.
6. Separately Carbopol was added to purified water and allowed to disperse uniformly under stirring.
7. Then the dispersion obtained in step 6) was added to the mixture of step 5), drop wise under stirring. Followed by mixing the resultant mixture and allowing cooling to the room temperature to obtain the product.

q.s. in the example is the amount of ingredient sufficient to give the desired effect to the final composition, in terms of stability, permeation and efficacy.

Example 8.2: Teriflunomide Topical Gels

| | Teriflunomide Topical gels | | | | | | |
|---|---|---|---|---|---|---|---|
| S. No | Name of the ingredient | Strength (% w/w) | | | | | |
| | | 0.5% w/w | 1.0% w/w | 2.0% w/w | 4.0% w/w | 6.0% w/w | 10.0% w/w |
| 1 | Teriflunomide | 0.50 | 1.00 | 2.00 | 4.00 | 6.00 | 10.00 |
| 2 | L- menthol | 5.00 | 5.00 | 5.00 | 5.00 | 5.00 | 5.00 |
| 3 | Labrafac PG | 5.00 | 5.00 | 5.00 | 5.00 | 5.00 | 5.00 |
| 4 | Geleol mono and diglycerides | q.s. | q.s. | q.s. | q.s. | q.s. | q.s. |
| 5 | Emulcire 61 WL 2659 | 3.00 | 3.00 | 3.00 | 3.00 | 3.00 | 3.00 |
| 6 | Gelot 64 | q.s. | q.s. | q.s. | q.s. | q.s. | q.s. |
| 7 | DMSO | 10.00 | 10.00 | 10.00 | 10.00 | 10.00 | 10.00 |
| 8 | Methyl paraben | 0.50 | 0.50 | 0.50 | 0.50 | 0.50 | 0.50 |
| 9 | propyl paraben | 0.10 | 0.10 | 0.10 | 0.10 | 0.10 | 0.10 |
| 10 | sodium thiosulfite | 0.20 | 0.20 | 0.20 | 0.20 | 0.20 | 0.20 |
| 11 | Carbopol | 0.80 | 0.80 | 0.80 | 0.80 | 0.80 | 0.80 |
| 12 | 10% NaOH Solution | 4.00 | 4.00 | 4.00 | 4.00 | 4.00 | 4.00 |
| 13 | Transcutol P | q.s. | q.s. | q.s. | q.s. | q.s. | q.s. |
| 14 | Purified water | 51.90 | 51.40 | 50.40 | 48.40 | 46.40 | 42.40 |
| | Total (%) | 100.00 | 100.00 | 100.00 | 100.00 | 100.00 | 100.00 |

Brief manufacturing process:
1. Teriflunomide was added to a mixture of Labrafac PG, geleol mono and dihydro glycerides, DMSO, L-Menthol and then the mixture was heated to 70-80° C. under continuous stirring.
2. After complete solubilization of the Teriflunomide, 10% NaOH solution was added to step 1 mixture under stirring, while maintaining the temperature at 70-80° C.
3. Followed which preservatives were added to the step 2 resultant.
4. Then to the resultant mixture of step 3) Emulcire 61 WL 2659 and gelot 64 were added.
5. Then Sodium thiosulfite was dissolved in purified water and Carbopol was dispersed in it, following which Transcutol-P was added to the carbopol dispersion.
6. After which step 4) mixture was cooled to 60° C. and was added to the step-5 dispersion drop wise under continuous stirring.
7. Then the resulting mixture of step 6 mixture was cooled to room temperature under continuous stirring and kept aside for few minutes to get solidified gel.

q.s. in the example is the amount of ingredient sufficient to give the desired effect to the final composition, in terms of stability, permeation and efficacy.

Example 8.3: Teriflunomide Topical Lotions

| | Teriflunomide Topical Lotions | | | | | | |
|---|---|---|---|---|---|---|---|
| S. No | Name of the ingredient | Strength (% w/w) | | | | | |
| | | 0.5% w/w | 1.0% w/w | 2.0% w/w | 4.0% w/w | 6.0% w/w | 10.0% w/w |
| 1 | Teriflunomide | 0.50 | 1.00 | 2.00 | 4.00 | 6.00 | 10.00 |
| 2 | L- menthol | 5.00 | 5.00 | 5.00 | 5.00 | 5.00 | 5.00 |
| 3 | Labrafac PG | q.s. | q.s. | q.s. | q.s. | q.s. | q.s. |
| 4 | Peceol | 12.00 | 12.00 | 12.00 | 12.00 | 12.00 | 12.00 |
| 5 | Emulcire 61 WL 2659 | 8.00 | 8.00 | 8.00 | 8.00 | 8.00 | 8.00 |
| 6 | Gelot 64 | q.s. | q.s. | q.s. | q.s. | q.s. | q.s. |
| 7 | DMSO | 10.00 | 10.00 | 10.00 | 10.00 | 10.00 | 10.00 |
| 8 | Methyl paraben | 0.50 | 0.50 | 0.50 | 0.50 | 0.50 | 0.50 |
| 9 | propyl paraben | 0.06 | 0.06 | 0.06 | 0.06 | 0.06 | 0.06 |
| 10 | sodium thiosulfite | 0.20 | 0.20 | 0.20 | 0.20 | 0.20 | 0.20 |
| 11 | 10% NaOH Solution | 4.00 | 4.00 | 4.00 | 4.00 | 4.00 | 4.00 |
| 12 | Transcutol P | 10.00 | 10.00 | 10.00 | 10.00 | 10.00 | 10.00 |
| 13 | Purified water | 35.34 | 34.84 | 33.84 | 31.84 | 29.84 | 25.84 |
| | Total (%) | 100.00 | 100.00 | 100.00 | 100.00 | 100.00 | 100.00 |

Brief manufacturing process:
1. Teriflunomide was mixed with Labrafac PG, Peceol, DMSO, L-Menthol and in a glass beaker and heated to 70-85° C. under continuous stirring.
2. After complete solubilization of the teriflunomide, 10% NaOH solution was added to the step 1) drug solution mixture.
3. Followed by addition of preservatives, methyl paraben and propyl parabens to the step 2 solution.
4. Then Emulcire 61 WL 2659 and gelot 64 were also added to above step 3) at the same conditions.
5. Separately Sodium thiosulfite was dissolved in purified water and transcutol-P was added to it.
6. Then Step 4) resultant was cooled to 60° C. and it was added to step-5) drop wise under continuous stirring.
7. Finally, the above step 6) resulting composition was cooled down to room temperature under continuous stirring and kept aside for few minutes to get lotion.
    q.s. in the example is the amount of ingredient sufficient to give the desired effect to the final composition, in terms of stability, permeation and efficacy.

All the compositions of present invention were found to be stable without any known impurity (2-Cyano N-[4-(trifluromethyl)phenyl]acetamide) or any single unknown impurity detected, and having comparatively better and significant permeation/diffusion for giving effective topical anti-inflammatory & pain relief therapy. The samples were evaluated for various parameters to check their permeation and diffusions.

We claim:
1. A topical pharmaceutical composition of
   (i) teriflunomide or its pharmaceutically acceptable salt in an amount of 0.5% to 10% by weight of the composition;
   (ii) a carrier comprising waterer;
   (iii) a permeation enhancer; and
   (iv) at least one pharmaceutically acceptable excipient;
   wherein the teriflunomide or its pharmaceutically acceptable salt to the permeation enhancer is in a weight ratio of 1:1 to 1:20.
2. The topical pharmaceutical composition as claimed in claim 1, wherein the excipient is selected from the group comprising solvents, co-solvents, emulsifiers, co-emulsifiers, solubilizers, preservatives, thickeners, pH modifiers, buffers, diluents, coolants, counter-irritants, surfactants, oil-phase components, aqueous phase components, anti-oxidants, moisturisers, lubricants, stabilizers and other topical excipients.
3. The topical pharmaceutical composition as claimed in claim 1, wherein the excipient is a lipophilic component or a hydrophilic component.
4. The topical pharmaceutical composition as claimed in claim 1, wherein the composition is in the form of a cream, a lotion, an ointment, a gel, a spray, a liniment, or a solution.
5. The topical pharmaceutical composition as claimed in claim 1, wherein the composition comprises teriflunomide or its pharmaceutically acceptable salt in the range of 0.5% to 5% by weight of the composition.
6. The topical pharmaceutical composition as claimed in claim 1, wherein the composition comprises the teriflunomide or its pharmaceutically acceptable salt to the permeation enhancer in a weight ratio of 1:1 to 1:10.
7. The topical pharmaceutical composition as claimed in claim 1, wherein the composition has a pH in the range between 3 and 8.
8. A topical pharmaceutical composition as claimed in claim 1, further comprising one or more active ingredients selected from the group consisting of
   a) COX inhibitors;
   b) Corticosteroids;
   c) Immuno-suppressants;
   d) Counter-irritants; and
   e) Antihistaminic agents.
9. The topical pharmaceutical composition as claimed in claim 1, wherein the composition is in the form of a cream.
10. The topical pharmaceutical composition as claimed in claim 1, wherein the composition is in the form of a lotion.
11. The topical pharmaceutical composition as claimed in claim 1, wherein the composition has a pH in the range between 4.5 and 7.5.
12. The topical pharmaceutical composition as claimed in claim 1, wherein the composition has a pH in the range between 5.0 and 6.5.
13. The topical pharmaceutical composition as claimed in claim 1, wherein the composition has a pH of about 5.5.
14. The topical pharmaceutical composition as claimed in claim 1, wherein the permeation enhancer comprises dimethyl sulfoxide.
15. A process for the preparation of the topical pharmaceutical composition as claimed in claim 1, comprising the following steps:
   i. combining an oily phase including an oil phase component with an aqueous phase including an aqueous phase component to provide a first mixture;
   ii. combining a second mixture comprising teriflunomide or its pharmaceutically acceptable salt and a carrier or a permeation enhancer with the first mixture to form the composition;
   iii. optionally adding one or more preservatives to the composition;
   iv. optionally adding one or more gelling agents to the composition;
   V. optionally adjusting the pH of the composition with a pH adjusting agent; and
   vi. wherein at least one of the oily phase, the aqueous phase, and the second mixture further comprises the at least one pharmaceutically acceptable excipient.
16. The process as claimed in claim 15, wherein at least one of the oily phase or aqueous phase further comprises an emulsifier.
17. The process as claimed in claim 15, further comprising adjusting the pH of the composition with a pH adjusting agent.
18. A topical pharmaceutical composition of
   (i) teriflunomide or its pharmaceutically acceptable salt;
   (ii) a carrier comprising water;
   (iii) a permeation enhancer; and
   (iv) at least one pharmaceutically acceptable excipient;
   wherein the teriflunomide or its pharmaceutically acceptable salt to the permeation enhancer is in a weight ratio of 1:1 to 1:10.
19. A topical pharmaceutical composition of
   (i) teriflunomide or its pharmaceutically acceptable salt in an amount of 0.5% to 15% by weight of the composition;
   (ii) a carrier comprising water;
   (iii) optionally a permeation enhancer; and
   (iv) at least one pharmaceutically acceptable excipient;
   wherein the teriflunomide or its pharmaceutically acceptable salt to the carrier is in a weight ratio of 1:1 to 1:20.

* * * * *